United States Patent [19]

Jefford

[11] Patent Number: 5,559,145
[45] Date of Patent: Sep. 24, 1996

[54] 1,2,4-TRIOXANE DERIVATIVES

[75] Inventor: Charles W. Jefford, Troinex, Switzerland

[73] Assignee: Oxaco S.A., Geneva, Switzerland

[21] Appl. No.: 479,948

[22] Filed: Jun. 7, 1995

Related U.S. Application Data

[63] Continuation-in-part of Ser. No. 327,224, Oct. 21, 1994, abandoned, which is a continuation of Ser. No. 186,812, Jan. 24, 1994, abandoned, which is a continuation of Ser. No. 53,294, Apr. 26, 1993, abandoned, which is a continuation of Ser. No. 926,553, Aug. 6, 1992, abandoned, which is a continuation of Ser. No. 759,712, Sep. 12, 1991, abandoned, which is a continuation of Ser. No. 528,028, May 23, 1990, abandoned, which is a continuation-in-part of Ser. No. 201,060, Jun. 1, 1988, abandoned.

[51] Int. Cl.$^6$ .................... A61K 31/335; C07D 323/04
[52] U.S. Cl. ........................ 514/452; 549/361; 549/364
[58] Field of Search .................... 549/361, 364; 514/452

[56] References Cited

FOREIGN PATENT DOCUMENTS 0286316  10/1988  European Pat. Off. .

*Primary Examiner*—Nicky Chan
*Attorney, Agent, or Firm*—L. Dan Tucker

[57] ABSTRACT

1,2,4-trioxane derivatives of formula:

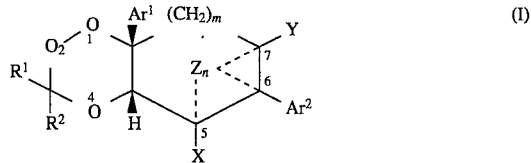

(wherein each of the subscripts m and n is equal to 0 or 1;

the symbol Z represents an epoxide oxygen atom at the 5,6 or 6,7 positions, or a pair of electrons forming a double bond at the 5,6 or 6,7 positions;

each of the symbols $Ar^1$ and $Ar^2$, being the same or different represents an aromatic group which optionally substituted;

each of the symbols $AR^1$ and $R^2$, being the same or different, represents a linear or branched alkyl group, which is optionally substituted, or $R^1$ and $R^2$, taken together with the carbon atom to which they are attached, form an alicyclic group which is optionally interrupted by one or more oxygen, sulphur or nitrogen atoms and which group is optionally substituted with one or more alkyl or aryl groups, or one or more functional groups; and each of X and Y, being the same or different, represents a hydrogen atom or a functional group which contains oxygen, nitrogen or sulphur) are of use in the treatment of tropical diseases including malaria and have other physiological activities.

12 Claims, No Drawings

1,2,4-TRIOXANE DERIVATIVES

This application is a continuation-in-part of Ser. No. 08/327,224, filed Oct. 21, 1994 abandoned, which is a continuation of Ser. No. 08/186,812, filed Jan. 24, 1994 abandoned which is a continuation of Ser. No. 08/053,294, filed Apr. 26, 1993 abandoned, which is a continuation of Ser. No. 07/926,553, filed Aug. 6, 1992 abandoned, which is a continuation of Ser. No. 07/759,712, filed Sep. 12, 1991, abandoned, which is a continuation of Ser. No. 07/528,028, filed May 23, 1990 abandoned which is a continuation-in-part of Ser. No. 07/201,060, filed Jun. 1, 1988, abandoned.

This invention relates to derivatives of 1,2,4-trioxane, and to pharmaceutical uses of the derivatives.

Tropical diseases such as malaria can be treated by nitrogen-containing agents, including quinine, chloroquine, mefloquine or pyrimethanine. Parasites (*Plasmodium falciparum*) resistant to such medicinal substances, in particular to chloroquine, have developed, making the fight against these diseases much harder.

Recently, a new antimalarial agent which is a polyoxygenated tetracyclic molecule has been isolated from the shrub *Artemisia annua* L and named "Qinghaosu" (see for example Science, 228. 1049 (1985). Qinghaosu has the structure:

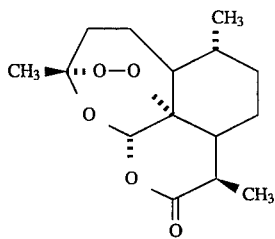

It is remarkably active against choloroquine-resistant strains of *P. falciparum*, but synthesis is difficult and commercially impractical. Presently, the only source of Qinghaosu is by extraction from crops of *Artemisia annua* L in small and variable yields.

SUMMARY OF THE INVENTION

It has now been discovered that a new class of purely synthetic compounds, in particular certain fused derivatives of 1,2,4-trioxane, exhibit interesting pharmaceutical properties, in particular anti-malarial properties.

This invention provides for the pharmaceutical use of a 1,2,4-trioxane derivative of formula:

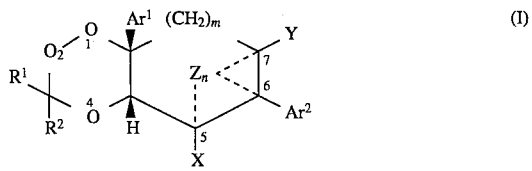

wherein
each of the subscripts m and n is equal to 0 or 1;
the symbol Z represents an epoxide oxygen a tom a t the 5,6 or 6,7 positions, or a pair of electrons forming a double bond at the 5,6 or 6,7 positions;
each of the symbols $Ar^1$ and $Ar^2$, being the same or different, represents an aromatic group which is optionally substituted;
each of the symbols $R^1$ and $R^2$, being the same or different, represents a linear or branched alkyl group, which is optionally substituted, or $R^1$ and $R^2$, taken together with the carbon atom to which they are attached, form an alicyclic group which is optionally interrupted by one or more oxygen, sulphur or nitrogen atoms and which group is optionally substituted; and
each of X and Y, being the same or different, represents a hydrogen atom or a functional group which contains oxygen, nitrogen or sulphur.

The present invention embraces racemic mixtures, as well as one or other of the enantiomeric forms.

PREFERRED EMBODIMENTS OF THE INVENTION

The compounds of this invention are of interest because of their synthetic origin. Representative compounds are particularly active as antimalarial agents, more so than chloroquine or mefloquine. From in vitro and in vivo tests, the present 1,2,4-trioxane derivatives exhibit equal or higher activity than Qinghaosu, in particular against chloroquine-resistant clones of *P. falciparum*. Some of the compounds have shown, according to appropriate tests, interesting immunosuppressive activity. Consequently, the compounds are of utility for the treatment of tropical diseases such as malaria, or for the treatment of diseases of immunological nature or viral origin.

Further examples of tropical diseases which now may be treated in accordance with this invention by 1,2,4-trioxanes include toxoplasmosis, leishmaniasis, pneumonitis, and onchocerciasis.

Infection with *Toxoplasma qondii*, a cosmopolitan protozoan parasite, produces only benign symptoms in normal individuals. The infection gives rise to toxoplasmosis, is a major hazard for immunocompromised patients, such as those suffering from acquired immune deficiency syndrome (AIDS), and pregnant women who become infected for the first Lime. A need remains for an effective drug which is less toxic than the most effective treatment currently available, either the synergistic combination of pyrimethamine with sulfonamides, or macrolide drugs such as erythromycin.

Infection with *Leishmania donovani*, a flagellate protozoa spread by sandflies, is the cause of Kala Azar, the systemic form of leishmaniasis affecting the blood, lymphatics, spleen and marrow.

Infection with *Pneumocystis carinii*, an opportunistic organism believed to be a protozoon, is the underlying cause of pneumonitis in immunocompromised hosts.

Infection with *Onchocerca volvulus*, a filarial worm, can lead to onchocerciasis or river blindness, which afflicts some 17 million people who live near fast-flowing water in Africa and Central and South America. It is one of the more damaging filarial parasites and effective measures are still awaited for its eradication. Furthermore, onchocerciasis in cattle remains a problem, rendering the meat unfit for human consumption.

Hence, the present Invention provides pharmaceutical compositions which comprise a compound of the formula (I), together with a pharmaceutically acceptable carrier.

The compounds of the present invention have very low toxicity, permitting massive doses to be given to patients at the brink of death. For example, the compounds can be formulated as suspensions in oil and injected intramuscularly as a single shot. While formulations for parenteral administration may be used, it is within this invention to formulate the compounds as formulations for oral administration. Tablets for prophylactic treatment are especially suitable. To this end, some modifications of the compounds may be desirable, for example to enhance water solubility through inclusion of p- or m- carboxyl or amino substituents onto the aryl substituents. Suitable modifications can be achieved by routine experiment tion, including for instance (i) etherification of a 5- or 7- hydroxy compound to give an alkyloxycarbonylmethyl ether which can be de-esterified to give a 5- or 7-oxymethylcarboxylic acid; (ii) synthesis of pyridinium derivatives by treating bis-pyridylcyclopentadiene with singlet oxygen and then a ketone $R^1R^2C=O$; (iii) synthesis of analogous compounds where $Ar^1$ and/or $Ar^2$ are p- or m-diethylaminophenyl substituents, followed by acidification to give a salt; or using other substituents on $Ar^1$ and/or $Ar^2$ for solubilization. More generally, formulation of the compounds of this invention can be based on the conventional techniques available to the pharmacist.

In the formula (I), the subscript m can be 0 to give a 5-membered ring, or 1 to give a 6-membered ring. In general, it is preferred that m is 0.

The subscript n can be 0 or 1/ When n is 1, the symbol Z represents a 5,6-epoxy group, a 6,7-epoxy group, a double bond at the 5,6 position, or a double bond at the 6,7 position. For preference, the subscript n is 1 and Z represents a double bond.

The symbols $Ar^1$ and $Ar^2$ represent the same or different aromatic groups, which may be heterocyclic aromatic groups, for instance with 5 or 6 ring atoms with 1 or 2 oxygen, sulphur or nitrogen heteroatoms. Examples of such aromatic groups include a phenyl, p-tolyl, naphthyl or pyridyl group. The aromatic groups can be substituted, for example, with one or more alkyl groups such as methyl, aryl groups such as phenyl; alkoxy groups such as methoxy, hydroxy groups: halogen atoms such as chlorine: or fluorine: carboxyl groups: optionally alkyl-substituted amino groups such as diethylamino groups; alkoxycarbonyl groups; or other functional groups. The carboxyl groups may be esterified.

The symbols $R^1$ and $R^2$ can be the same or different alkyl groups, especially alkyl groups of 1 to 4 carbon atoms, in particular methyl, ethyl or n-butyl, which are optionally substituted for example with the substituents illustrated for the aromatic groups $Ar^1$ and $Ar^2$. Alternatively, $R^1$ and $R^2$ with the carbon atom to which they are attached can form an alicyclic group, optionally interrupted with O, S, S=O, $S(=O)_2$ or NH, and optionally substituted for example with the substituents illustrated for $Ar^1$ and $Ar^2$, especially a cycloalkane of 3 to 7 carbons optionally interrupted with O or S, and optionally substituted with hydroxy or methyl, in particular a cyclopentane, cyclohexane or oxolane group.

The groups X and Y are the same or different, and each represents a hydrogen atom or a functional group which contains oxygen, nitrogen or sulphur. For preference, at least one of X and Y is a hydrogen atom. Examples of functional groups include a hydroxy group, a peroxide group, an ester (such as an optionally chiral oxycarbonyl, oxycarbonyloxy or oxyalkylcarbonyloxy ester), a carboxylic acid (such as an oxyalkylcarboxylic acid), a ketone, an imine, a hydrazone, an amino acid, a peptide residue, a glycosyl group, a phosporyl group, a diphosphenyl group, or a phosphate reside.

Preferred compounds of formula (I) include those listed in the following table:

TABLE

Part (i)

| code | m | n | Z* | $R^1$ | $R^2$ |
|---|---|---|---|---|---|
| 1 skdj-25 | 0 | 1 | 5,6= | $CH_3$ | $CH_3$ |
| 2 skdj-44 | 0 | 1 | 6,7= | $CH_3$ | $CH_3$ |
| 3 skdj-41 | 0 | 1 | 5,6O | $CH_3$ | $CH_3$ |
| 4 skdj-30 | 0 | 1 | 5,6= | | $-(CH_2)_4-$ |
| 5 aj-30 | 0 | 1 | 5,6= | | $-(CH_2)_5-$ |
| 6 aj-12 | 0 | 1 | 5,6= | $CH_3$ | $CH_3$ |
| 7 aj-21 | 0 | 1 | 6,7= | $CH_3$ | $CH_3$ |
| 8 aj-18 | 0 | 1 | 6,7= | $CH_3$ | $CH_3$ |
| 9 aj-04 | 0 | 1 | 6,7= | $CH_3$ | $CH_3$ |
| 10 aj-19 | 0 | 1 | 6,7= | $CH_3$ | $CH_3$ |
| 11 aj-44 | 0 | 1 | 6,7= | | $-(CH_2)_4-$ |
| 12 jcr-pm4 | 0 | 1 | 5,6= | | $-(CH_2)_2O(CH_2)_2-$ |
| 13 jcr-pm5 | 0 | 1 | 6,7= | | $-(CH_2)_5-$ |
| 14 jcr-pm3 | 0 | 1 | 5,6= | | $-(CH_2)_6-$ |
| 15 jcr-pm8 | 0 | 1 | 6,7= | | $-(CH_2)_5-$ |
| 16 jcr-pm7 | 0 | 1 | 6,7= | | $(CH_2)_5-$ |
| 17 jcr-419 | 0 | 1 | 5,6= | | $-(CH_2)_2CO(CH_2)_2-$ |
| 18 jcr-423 | 0 | 1 | 5,6= | $-CH_3$ | $-(CH_2)_3COOEt$ |
| 19 jcrgc2 | 1 | 1 | 5,6= | | $-(CH_2)_4-$ |
| 20 jcrgc11 | 0 | 1 | 5,6= | | $-CH_2)_2C(CH_2)_2-$ $O(CH_2)_2O$ |
| 21 jcrpm-2 | 0 | 1 | 5,6= | $CH_3$ | $C_2H_5$ |

Part (ii)

| code | X | Y | $Ar^1$ | $Ar^2$ |
|---|---|---|---|---|
| 1 skdj-25 | H | H | Ph | Ph |
| 2 skdj-44 | OH | H | Ph | Ph |
| 3 skdj-41 | H | H | Ph | Ph |
| 4 aj-30 | H | H | Ph | Ph |
| 5 aj-31 | H | H | Ph | Ph |
| 6 aj-12 | H | H | p-ClPh | p-ClPh |
| 7 aj-21 | OCO(o-F)Ph | H | Ph | Ph |
| 8 aj-18 | O—CO—O—CH(CH$_3$)$_2$ | H | Ph | Ph |
| 9 aj-04 | =O | H | Ph | Ph |
| 10 aj-19 | OCOCH$_2$CH(CH$_3$)$_2$ | H | Ph | Ph |
| 11 aj-44 | OH | H | Ph | Ph |
| 12 jcr-pm4 | H | H | Ph | Ph |
| 13 jcr-pm5 | OOH | H | Ph | Ph |
| 14 jcr-pm3 | H | H | Ph | Ph |
| 15 jcr-pm8 | =O | H | Ph | Ph |
| 16 jcr-pm7 | OH | H | Ph | Ph |
| 17 jcr-419 | H | H | Ph | Ph |
| 18 jcr-423 | H | H | Ph | Ph |
| 19 jcrgc2 | H | H | Ph | Ph |
| 20 jcrgc11 | H | H | Ph | Ph |
| 21 jcrpm-2 | H | H | Ph | Ph |

Z*: in the table, "5,6" and "6,7", refer respectively to the bond between the 5 and 6 positions, and the 6 and 7 positions. A double bond is shown "=". An epoxide is shown "O".

Especially preferred compounds are numbers 12, 16 and close analogues thereof.

The compounds 1, 2, 4 and 19 listed above are known from the scientific literature, without mention of any pharmaceutical properties (see on this subject Helv Chim Acta. 69, 941 (1986) and J. Chem. Soc., Chem Comm., 523 (1984)).

Most of the compounds of formula (I) are new and can be synthesized by analogy with their previously described homologues, with the aid of conventional techniques.

The new derivatives of 1,2,4-trioxane may be represented by means of the following formula:

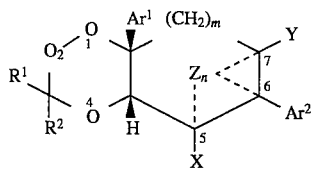

in which m, n, Ar¹, AR², R¹, R², X, Y and Z are as defined for the formula (I), with the exception of the following compounds:

$\underline{m}$ = 0 or 1; $\underline{n}$ = 1; Z = 5,6=; R¹ = R² = —CH₃ or R¹ + R² = —(CH₂)₄—; X = Y = H; Ar¹ = Ar² = Ph.     (a)

$\underline{m}$ = O; $\underline{n}$ = 1; Z = 5,6=; R¹ = R² = —CH₃; X = —OOH or —OH; Ar¹ = Ar² = Ph.     (b)

The present invention provides a process for preparing the compounds of formula (I), which comprises reaction of a ketone R¹R²=O with a compound of formula:

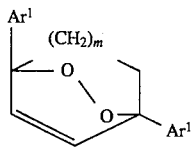

to give a compound of formula (III):

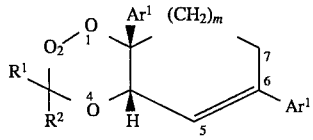

followed by derivatization as necessary.

Derivatization can follow the methods given in the literature, involving for example epoxidation of the olefin, or conversion of the 5,6-olefin (III) with singlet oxygen to a 5-peroxy-6,7-olefin, thence hydro borohydride reduction to a 5-hydroxy-6,7-olefin, and oxidation to a 5-keto-6,7-olefin. The 5-keto-6,7-olefin can be reacted with an amine $R^aNH_2$ to give an imine, with a hydrazine $NH_2NR^bR^c$ to give a hydrazone, or catalytically reduced to remove the keto group giving the 6,7-olefin, which can thereafter be reduced to remove the olefinic unsaturation. The 6,7-olefin can itself be derivatized to give isomers of the derivatives mentioned above in the derivatization of the 5,6-olefin.

If desired, the ketone R¹R²C=O can be alicyclic and/or a pure optical isomer. The use of chiral ketones such as (—)camphor, carvone, pulegone or menrhone enables stereospecific synthesis of a chiral product.

The 5,6-olefin (III) can also be oxidized at the allylic methylene group to give the corresponding a,ö-unsaturated ketone and thence the alcohol by reduction. The aforementioned hydroxy groups can be converted to useful esters.

EXAMPLES OF THE INVENTION

The present invention is illustrated by the following Examples for synthesis of new compounds, and in vitro test data for the anti-malarial activity of the new and known compounds as well as their immuno-modulatory activity. On the basis of the given information, a practitioner in the field will be able to develop the most appropriate derivatives and select the doses needed for the in vivo treatment of the diseases in question.

EXAMPLE 1

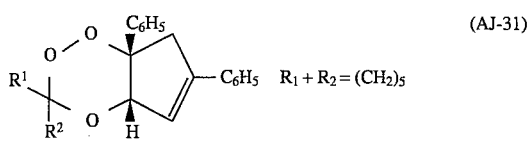

This compound was prepared from 1,4-diphenyl-1,4-epidioxycyclopent-2-ene and cyclohexanone, according to the method published in J Chem Soc Chem Comm 523, (1984), in the presence of trimethylsilyl trifluoromethanesulfonate as catalyst in CH₂Cl₂ at around −78° C. The reaction mixture was treated with triethylamine and washed with water to give the product which was finally purified by recrystallization from a mixture of cyclohexane/dichloromethane, giving yellow crystals mp 102°–103° C. in a yield of 84%.

NMR (360 MHz, CDCl): w=1.3–1.8 (8H); 1.87 (1H); 2.13 (1H); 2.98 (1H, 3.30 (1H, d); 5.16 (1H); 6.37 (1H, d); 7.34 (6H); 7.50 (2H, d); 7.61 (2H, d).

MS (m/e) =348 (0,2]M+), 233 (4), 218 (20), 105 (100), 91 (10), 77 (25), 55 (12).

EXAMPLE 2

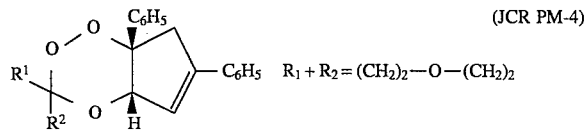

This compound was prepared according to the method defined in Example 1. The cyclohexanone was replaced by an equivalent portion of 4-oxacyclohexanone. After addition of triethylamtne to the reaction mixture, chromatography on silica gel and recrystallization from acetonitrile, colourless crystals were obtained, mp 145°–60° C., in a yield of 59%.

NMR (360 MHz, CDCl₃): w=1.75 (2H); 2.09 (1H); 2.30 (1H); 3.05 (d, 1H); 3.31 (d, 1H); 3.65–3.86 (4H); 5.24 (1H); 6.35 (1H); 7.28–7.45 (6H); 7.48 (2H); 7.59 (2H).

MS (m/e)=350 (0.4; M⁺), 218 (17), 105 (100), 77 (30).

EXAMPLE 3

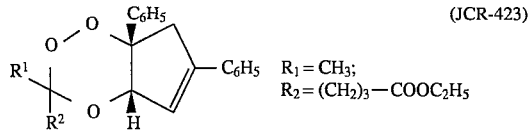

This compound was prepared according to the method defined in Example 1. The cyclohexanone was replaced by an equivalent portion of ethyl 5-oxohexanoate. After purification by chromatography silica gel and recrystallization, a yellow oil was obtained in a yield of 34% (mixture of 2 epimers)

NMR (200 MHz, CDCl₃): w=1.22 (3H); 1.30 (3H); 1.59 (3H); 1.65–2.10 (4H); 2.33 (2H); 2.98 (d, 1H); 3.30 (d, 1H); 4.08 (2H); 4.98 (1H); 5.07 (1H); 6.38 (1H); 7.28–7.59 (10H).

IR (CCl₄): $n_{max}$=1740 cm⁻¹

EXAMPLE 4

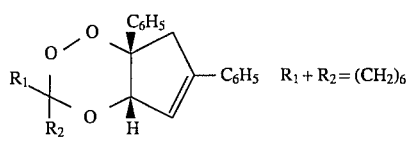

(JCR-PM-3)

$R_1 + R_2 = (CH_2)_6$

This compound was prepared according to the method defined in Example 1. The cyclohexanone was replaced by an equivalent portion of cycloheptanone, and purification by chromatography over silica gel to give colourless crystals, mp 55°–60° C., yield 53%.

NMR (360 MHz, CDCl₃): w=1.37–1.76 (9H); 1.95 (2H); 2.37 (1H); 2.99 ( d, 1H); 3.33 (d, 1H); 4.92 (1H); 6.38 (1H); 7.26–7.43 (6H); 7.51 (2H); 7.56 (2H).

MS (m/e)=250 (7), 218 (15), 105 (100), 77 (37), 68 (16), 55 (25).

EXAMPLE 5

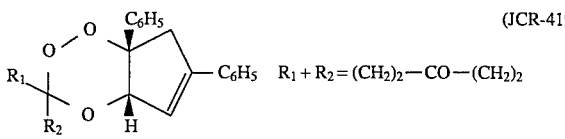

(JCR-419)

$R_1 + R_2 = (CH_2)_2 — CO — (CH_2)_2$

This compound was prepared from 1,4-diphenyl-1,4-epidioxycyclopent-2-ene and cyclohexane-1,4-dione according to the method described in Example 1 and purification by chromatography over silica gel and recrystallization from a mixture of petroleum ether/diethyl ether gave colourless crystals mp 100°–101° C., yield 38%.

NMR ( 200 MHz, CDCl₃): w=1o97–2.70 (SH); 3.05 (d, 1H); 3.31 (d, 1H); 5.24 (1H); 6.36 (1H); 7.28–7.55 (SH); 7.60 (2H).

IR (CCl₄): $n_{max}$=1725 cm⁻¹

EXAMPLE 6

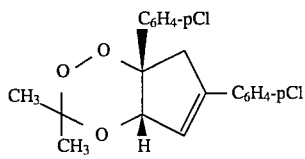

(AJ-12)

This compound was prepared according to the method described in Example 1, from acetone and 1,4-di-(p-chlorophenyl)-1,4-epidioxy- cyclopent-2-ene. The resulting crude reaction product was purified by recrystallization from a mixture of hexane/dichloromethane as colourless crystals mp 95°–96° C.; yield 78%.

NMR (360 MHz, CDCl₃): w=1.24 (3H); 1.52 (3H); 2.85 (d, 1H); 3.21 (d, 1H); 4.92 (1H); 6.31 (1H); 7.35 (6H); 7.47 (2H).

MS (m/e)=286(5), 139(100), 111(27), 75(8).

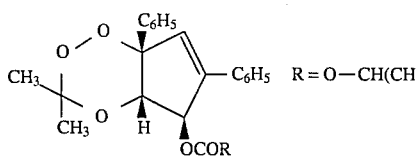

(AJ-18)

$R = O—CH(CH_3)_2$

This compound was prepared from the corresponding alcohol derivative (se Helv Chim Acta 69, 941 1986), after treatment of the latter with isopropyl chloroformate in the presence of pyridine at 0° C. After washing with water, the desired product was purified by recrystallization from hexane as colourless crystals mp 66.5–67.5° C., yield 79%.

NMR (360 MHz, CDCl₃): w=1.21 (6H); 1.42 (3H); 1.51 (3H); 4.46 (1H); 4.91 (1H); 6.32 (m, 2H); 7.40 6H); 7.53 (2H); 7.62 (2H).

IR (CCl₄): n max=1748 cm⁻¹

EXAMPLE 8

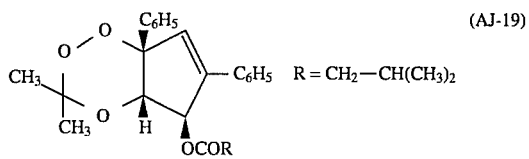

(AJ-19)

$R = CH_2—CH(CH_3)_2$

This compound was prepared according to the method described in Example 7, except that isopropyl chloroformate was replaced by an equivalent portion of isovaleryl chloride. The product was purified by recrystallization from a mixture of hexane/dichloromethane as colourless crystals mp 97°–80° C., yield 87%.

NMR (360 MHz, CDCl₃): w=0.75 (6H): 1.46 (3H): 1.47 (3H); 1.88 (1H); 2.07 (2H); 4.30 (1H); 6,36 (1H); 6.39 (1H); 7.40 (6H>; 7.51 (2H>; 7.61 (2H).

IR (CCl₄) :on max=1743 cm⁻¹

EXAMPLE 9

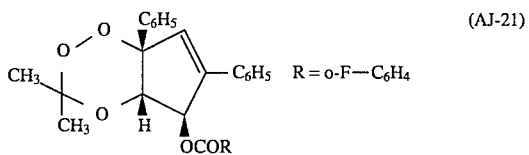

(AJ-21)

$R = o\text{-}F—C_6H_4$

This compound was prepared according to the method described in Example 7, except that isopropyl chloroformate was replaced by an equivalent portion of o-fluorobenzoyl chloride and the reaction product was purified by recrystallization from a mixture of hexane/dichloromethane as colourless crystals mp 113.5°–114° C., yield 81%.

NMR (360 MHz, CDCl₃): w=1.45 (3H); 1.50 (3H); 4.45 (1H); 6.47 (1H); 6.62 (1H); 7.09 (2H); 7.31–7.72 (12H).

IR (CCl₄): $n_{max}$ 1723 cm⁻¹

EXAMPLE 10

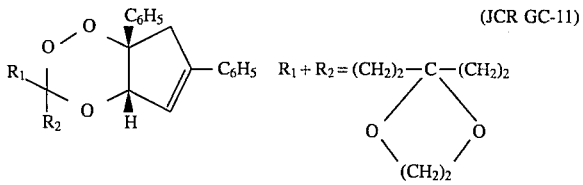

(JCR GC-11)

$R_1 + R_2 = (CH_2)_2—C—(CH_2)_2$

This compound was prepared from the compound of Example 5, by reaction of the latter with 1,2-di-( trimethylsiloxy)ethane, in the presence of trimethylsilyl trifluoromethanesulfonate as a catalyst (solvent CH₂Cl₂, temperature about −78° C.). The purification was effected by chromatography over silica gel to give colourless crystals mp 126°–129° C.; yield 93%.

NMR; (200 MHz, CDCl₃): w=1.40–2.50 (8H); 3.00 (d, 1H); 3.28 (d, 1H); 3.37–3° 90 (4H); 5.17 (1H); 6.34 (1H); 7.22–7.65 (10H).

EXAMPLE 11

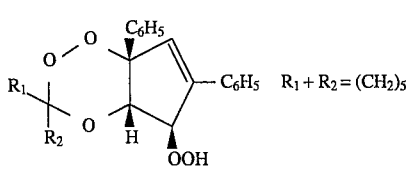
(JCR PM-5)
$R_1 + R_2 = (CH_2)_5$

This compound was prepared from the compound of Example 1, by treating the latter with singlet oxygen (see on this subject Helv Chim Acta 69, 941 (1986)) and purification by chromatography over silica gel to give colourless crystals mp 70° C., yield 90%.

NMR (200 MHz, CDCl$_3$): w=1.35–2.00 (10H); 4.76 (1H); 5.59 (1H); 6.38 (1H); 7.28–7.45 (6H); 7.62 (4H); 8.05 (1H).

IR (CCl$_4$): n$_{max}$=3545, 3460 cm$^{-1}$

EXAMPLE 12

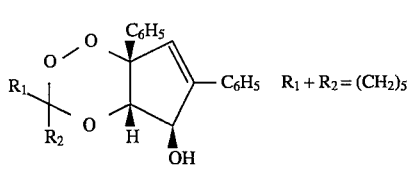
(JCR PM-7)
$R_1 + R_2 = (CH_2)_5$

This compound was prepared by reduction of the compound in Example 11 using sodium borohydride, and purification by recrystallization from a mixture of pentane/dichloromethane to give colourless crystals, yield 93%.

NMR (200 MHz, CDCl$_3$): w=1.35–2.03 (11H); 4.42 (1H); 5.26 (1H); 6.30 (d, 1H); 7.30–7.48 (6H); 7.65 (4H)

IR (CCl$_4$): n$_{max}$=3612, 3465 cm$^{-1}$

EXAMPLE 13

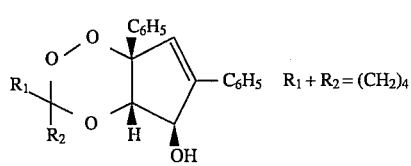
(AJ-44)
$R_1 + R_2 = (CH_2)_4$

This compound was prepared from the corresponding hydroperoxide, according to the method described in Example 12, and purification by chromatography over silica gel to give colourless crystals mp 103°–104° C., yield 93%.

NMR (360 MHz, CDCl$_3$): w=1.63–1.91 (6H); 2.05 (2H); 2.21 (1H); 4.43 (1H); 5.28 (1H); 6.38 (1H); 7.33–7.47 (6H); 7.62 (2H); 7.68 (2H).

IR (CCl$_4$): n$_{max}$=3620 cm$^{-1}$

EXAMPLE 14

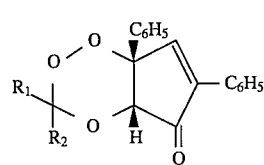
(AJ-04)

This compound was prepared from the corresponding hydroperoxide (see on this subject Helv. Chim. Acta 69, 941 (1986)), by treatment of the latter with acetic anhydride in the presence of triethylamine and purification by chromatography over silica gel followed by recrystallization from a mixture of hexane/dichloromethane to give colourless crystals mp 130°–131° C., yield 83%

NMR (360 MHz, CDCl$_3$): w=1.47 (3H); 1.70 (3H); 4.40 (1H); 7.47 (6H); 7.60 (2H); 7.72 (1H); 7.88 (2H).

IR (CCl$_4$): n$_{max}$=1732 cm$^{-1}$

EXAMPLE 15

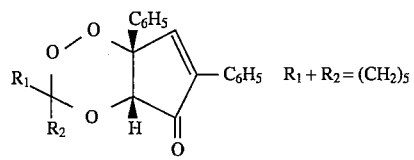
(JCR PM-8)
$R_1 + R_2 = (CH_2)_5$

This compound was prepared from the compound of Example 11, according to the method described in Example 14 giving colourless crystals, yield 30%.

NMR (200 MHz, CDCl$_3$): w=1.12–2.31 (10H); 4.41 (1H); 7.48 (6H); 7.61 (2H); 7.70 (1H); 7.89 (2H).

IR (CCl$_4$): n$_{max}$=1730 cm$^{-1}$

EXAMPLE 16

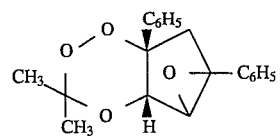
(SK DJ-41)

This compound was prepared by epoxidation of the corresponding olefin (see Helv Chim Acta 69, 941 (1986)) and purification by chromatography on silica gel, followed by recrystallization from a mixture of hexane dichloromethane giving colourless crystals of mp 88°–92° C., yield 84% (2 conformers).

MS (m/e)=147 (17), 105 (100), 77 (43).

EXAMPLE 17

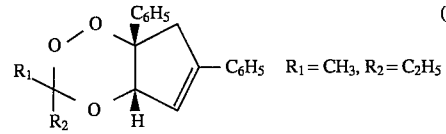
(JCR PM-2)
$R_1 = CH_3, R_2 = C_2H_5$

This compound was prepared from 1,4-diphenyl-1,4-epidioxycyclopent-2-ene and ethylmethyl ketone according to the procedure described in Example 1, and purified by chromatography over silica gel. A yellow oil was obtained in 80% yield (mixture of 2 epimers according to spectral analysis).

NMR (360 MHz, CDCl$_3$); w=0.99 (b, 3H); 1.30 (s, 3H); 1.88 (m, 1H); 2.07 (m, 1H); 2.98 (d, 1H); 3.31 (1H); 5.01 (s, 1H); 6.37 (1H, m); 7.29–7.42 (m, 6H); 7.50 (m, 2H>; 7.57 (m, 2H).

MS: m/e=218 (36), 157 (8), 128 (11), 115 (22), 105 (100), 77 (24).

Determination of in vitro anti-malarial activities

Determination of anti-malarial activity of the compounds was effected according to the methods published by R E Desjardins et al and W K Milhous et al (Desjardins, R. E., C. J. Cranfield, D. E. Haynes, and J. D. Chulay. 1979. Quantitative assessment of anitmalarial activity in vitro by a semiautomated microdilution technique. Antimicrob. Agents Chemother. 16:710–718. Milhous, W. K., N. F. Weathericy, J. H. Bowdre, and R. E. Desjardins. 1985. In vitro activities of and mechanisms of resistance to antifol antimalarials. Antimicrob. Agents Chemother. 27:525–530).

For such determinations, the following clones of *Plasmodium falciparum* were used:

chloroquine-resistant clone: Indochina-W2 (IndCh-W2)

chloroquine-sensitive clone: Sierra Leone-D6 (SL-D6)

The activity measured was then compared as indexes under the same conditions to the activity of Qinghaosu (I-QHS) and chloroquine (I-CHLQ), respectively. The indexes (I) provide a measure of the activity of the 1,2,4-trioxane derivatives tested in relation to the activity of the known anti-malarial substances.

The results of the determinations are summarized in the tables below.

EXAMPLE 18

The known compounds shown on the next page were synthesised by the indicated literature method.

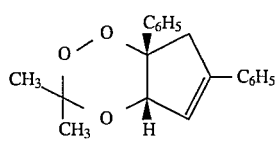

(SK DJ-25)
Helv. Chim. Acta
69, 941 (1986)

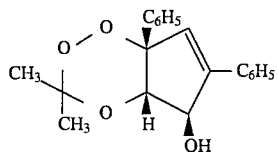

(SK DJ-44)
Helv. Chim. Acta
69, 941 (1986)

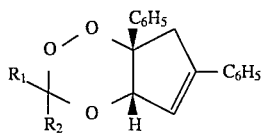

(AJ-30)
$R_1 + R_2 = (CH_2)_4$
J. Chem. Soc. Chem.
Comm. 523, 1984

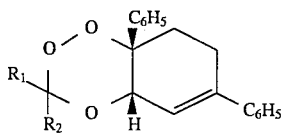

(JCR GC-2)
$R_1 + R_2 = (CH_2)_4$
J. Chem. Soc. Chem.
Comm. 523, 1984

TABLE No. 1

| Compound | IndCh-W2(IC$_{50}$) | |
|---|---|---|
| | I-QHS | I-CHLQ |
| 1 | 0.13 | 5.7 |
| 2 | 0.12 | 5.4 |
| 3 | 0.11 | 4.6 |
| 4 | 2.1 | 12.2 |
| 5 | 0.26 | 1.5 |
| 6 | 0.04 | 0.24 |
| 7 | 0.04 | 1.6 |
| 8 | 0.10 | 4.2 |
| 9 | 0.08 | 3.5 |
| 10 | 0.04 | 1.7 |
| 11 | 4.7 | 73.8 |
| 12 | 18.7 | 295.3 |
| 13 | 2.2 | 33.9 |
| 14 | 0.27 | 4.3 |
| 15 | 3.5 | — |
| 16 | 1.6 | — |
| 17 | 2.1 | — |
| 18 | 0.09 | — |
| 19 | 0.009 | 0.27 |
| 20 | 0.67 | — |
| 21 | 0.075 | — |

TABLE No. 2

| Trioxane | S6-D6(IC$_{50}$) | |
|---|---|---|
| | I-QHS | I-CHLQ |
| 1 | 0.18 | 0.20 |
| 2 | 0.25 | 0.27 |
| 3 | 0.13 | 0.14 |
| 4 | 0.79 | 0.82 |
| 5 | 0.20 | 0.20 |
| 6 | 0.06 | 0.06 |
| 7 | 0.05 | 0.06 |
| 8 | 0.16 | 0.18 |
| 9 | 0.20 | 0.21 |
| 10 | 0.09 | 0.10 |
| 11 | 1.85 | 1.16 |
| 12 | 1.10 | 0.67 |
| 13 | 1.47 | 0.93 |
| 14 | 0.13 | 0.08 |
| 15 | 1.93 | — |
| 16 | 0.49 | — |
| 17 | 1.06 | — |
| 18 | 0.28 | — |
| 19 | 0.02 | 0.008 |
| 20 | 0.39 | — |
| 21 | 0.36 | — |

Certain derivatives of 1,2,4-trioxane listed below were tested against mefloquine-resistant clones of Plasmodium falciparum (MEF-W2), according to the method previously cited.

TABLE No. 3

| Trioxane | MEF-W2(IC$_{50}$) |
|---|---|
| | I-QHS |
| 1 | 0.15 |
| 2 | 0.10 |
| 3 | 0.05 |

Determination of immunosupressive activity

Several of the compounds mentioned in Examples 1 to 17 were also tested for immunomodulatory activity (in vitro mitogenic assay; mixed lymphocyte reaction). The most important activity was exhibited by the compounds of Examples 2 and 6.

FURTHER EXAMPLES OF THE INVENTION

Determination of activity against other tropical diseases

The present invention is also illustrated by the following Further Examples for in vitro test data for the activity of the compounds in their use in treatment of toxoplasmosis, leishmaniasis, and onchocerciasiso In these tests, comprising Further Examples 1 to 3, a different numbering system is employed to identify the compounds, compared to the previous Examples. The compounds in Further Examples 1 to 3 are identified by reference to the following Table 4:

TABLE 4

| Compound | formula* | R$^1$ | R$^2$ |
|---|---|---|---|
| 1 | (Ia) | —(CH$_2$)$_4$— | |
| 2 | (Ia) | —(CH$_2$)$_2$S(CH$_2$)$_2$— | |
| 3 | (Ia) | —(CH$_2$)$_2$O(CH$_2$)$_2$— | |

TABLE 4-continued

| Compound | formula* | R¹ | R² |
|---|---|---|---|
| 4 | (Ia) | $-(CH_2)_2CO(CH_2)_2-$ | |
| 5 | (Ia) | $-CH_3$ | $-CH_3$ |
| 6 | (Ib) | $-(CH_2)_5-$ | |
| 7 | (Ic) | $-(CH_2)_2O(CH_2)_2-$ | |
| 8 | (Ic) | $-(CH_2)_4-$ | |
| 9 | (Ic) | $-(CH_2)_5-$ | |
| 10 | (Id) | $-(CH_2)_4-$ | |
| 11 | (Ie) | $-(CH_2)_5-$ | |
| 12 | (If) | $-CH_3$ | $-CH_3$ |

*where the formulae (Ia), (Ib), (Ic), (Id), (Ie), (If) are as follows
(in which Ph indicates a phenyl substituent and Tol indicates a tolyl substituent):

(Ia) 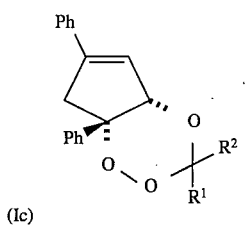 (Ib) 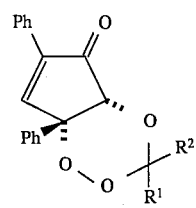

(Ic) 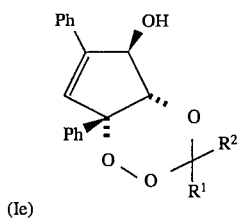 (Id) 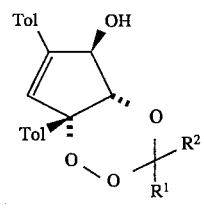

(Ie) 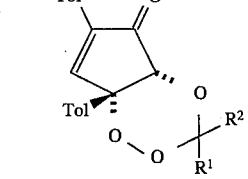 (If) 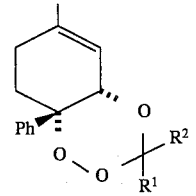

Further Example 1: activity against *Toxoplasmosis gondii*

(a) within macrophages, assessed by radioactivity studies

Unelicited murine peritoneal macrophages obtained by washing the peritoneal cavities of Swiss-Webster mice with 3 ml of Hanks' Balanced Salt Solution (HBSS) (4° C.) containing 5 U ml of heparin were purified by centrifugation in Ficoll-Paque (Pharmacia) 500×g for 15 min, pooled and suspended in medium 199 (M199) containing 10% heat-inactivated (56° C. for 60 min) fetal calf serum (FCS). An amount of 3×10% cells was seeded into each well of 96-well dishes (Costar) and allowed to adhere during 2–3 h at 37° C. in an 5% $CO_2$-95% air atmosphere. The nonadherent cells were removed by washing twice with prewarmed HBSS and challenged with 3 ×10 tachyzoites of the RG strain of *Toxoplasmosis gondii* in M199-3% FCS for 1 h. After washing twice with HBSS, the infected monolayers received the test drugs (Compounds 1 to 10 of Table 1) at various concentrations in M199-10% FCS. The monolayers were then pulsed with 2.5 mCi of [3H]uracil (Amersham) during a period of 18 h. The acid-precipitable radioactivity on each well was counted by using a filtration procedure and the $IC_{90}$ was calculated by probit analysis. The results are shown in the following Table 5:

TABLE 5

| | Inhibitory concentration (IC) mg ml⁻¹ | |
|---|---|---|
| Compound no | $IC_{50}$ | $IC_{90}$ |
| 1 | 2 | 6.8 |
| 2 | 1.7 | 5.3 |
| 3 | 106 | 260 |
| 4 | 285 | ï1000 |
| 5 | — | — |
| 6 | 26 | 54 |
| 7 | 580 | ï1000 |
| 8 | — | — |
| 9 | 420 | 850 |
| 10 | — | — |

(where "-" indicates not active up to 484 mg ml⁻¹)

It can be seen that the Compounds 1 and 2 were the most active, with 90% inhibitory concentrations ($IC_{90}$) at 6.8 and 5.3 mg ml⁻¹, respectively.

(b) within macrophages, assessed by light microcroscopy $2\times10^6$ of the macrophage cells were seeded into each chamber of four-chamber glass slides (Lab-Tek). After removing nonadherent cells with HBSS, the monolayers were infected with $2\times10^6$ *T. gondii* for 1 h followed by addition of the drugs with the media over 18 h. Monolayers were fixed with 0.4% 9-aminoacridine (50% ethanol-water vol/vol), Giemsa-stained, and assessed by light microscopy. The results are shown in the following Table 6, including results of control compounds:

TABLE 6

| Drug | (mg ml⁻¹) | % infected cells | Mean *T. gondii* per infected vacuole | *T. gondii* per 100 cells |
|---|---|---|---|---|
| none | 0 | 42 | 4.3 | 191 |
| 1 | 6.8 | 19 | 1.6 | 38 |
| 2 | 5.3 | 14 | 1.2 | 35 |
| 6 | 54 | 20 | 1.9 | 43 |
| P | 1 | 14 | 1.2 | 33 |
| P + S | 0.1 ± 25 | 18 | 1.9 | 42 |

P: pyrimethamine
P + S: pyrimethamine in combinatin with sulfadiazine

Thus, microscopic examination of the infected macrophages after treatment with compounds 1, 2 and 6 at their respective $IC_{90}$ values confirmed the inhibition of the intracellular growth of toxoplasma. This activity was comparable to that of pyrimethamine, and pyrimethamine in combination with sulfadiazine.

Control experiments indicated that at concentrations up to four times their $IC_{90}$ values the 1,2,4-trioxanes affected neither the viability of uninfected macrophages as assessed by morphological criteria and trypan blue dye exclusion test nor the viability of extracellular *T. gondii*, as judged by their ability to reinfect macrophages.

(c) within HeLa cells, assessed by light microcroscopy

Confluent epithelium-like HeLa (ATCC CCL2) cell monolayers growing on 6-well plastic multidish (9.6 cm², Nunc, Roskilde, Denmark) were used. After washing with HBSS, the monolayers were infected with $3\times 10^6$ ml$^{-1}$ *T. gondii* in M199-3% FCS (total amount per well, 3 ml) for 1 h, washed twice with HBSS, and the drugs were added with M199-10% FCS over 22 h. Monolayers were then fixed, Giemsa-stained and-assessed by light microscopy. The results are shown in the following Table 7:

TABLE 7

| Drug | (mg ml$^{-1}$) | % infected cells | Mean *T. gondii* per infected vacuole | *T. gondii* per 100 cells |
|---|---|---|---|---|
| none | 0 | 49 | 8.1 | 620 |
| 1 | 6.8 | 23 | 1.8 | 46 |
| 2 | 5.3 | 23 | 1.3 | 38 |

Since the compounds 1 and 2 were able to block parasite growth when *T. gondii* was harboured by cells of an epithelium-like cell line (HeLa), it follows that the antitoxoplasmic activity of the 1,2,4-trioxanes was not caused by a macrophage-specific mechanism, such as respiratory burst. Moreover, macrophages pre-incubated with different concentrations of 1,2,4-trioxanes, during 24 h, did not become activated and were not able to restrict the multiplication of *T. gondii* without the presence of the 1,2,4-trioxanes (data not shown).

Further Example 2: activity against *Onchocerca gutturosa*

Testing in vitro against *Onchocerca gutturosa* is a valid model for activity against *Onchocerca volvulus*.

(a) assessed by motility

Testing of test drugs (Compounds 1, 2, 3, 4, 5, 7, 8, 9, 11, and 12 of Table 1 ) against the parasitic worms *Onchocerca gutturosa* was carried out in accordance with the method described in J Helminth (1987) 60, 271, firstly using parasites, medium, serum, cells and test drugs.

The most striking result was shown by Compound 9, which immediately immobilized worms in less than a day. Compounds 4, 5, and 11 were also significantly effective at a day's exposure. In comparison, artemisinin was ineffective, while arteether reduced motility only by 30% after a day. On two to three days exposure, Compounds 2, 8, 9 and 12 were also markedly inhibitory. After an induction period, compounds 1 and 7 completely stopped morality, in 7 days. Thus, after 7 days, Compounds 1, 2, 4, 5, 7, 8, 9, 11 and 12 had reduced motility by 100%. Compound 3 was not so effective in this test.

These results compared favorably with those reported under the same conditions for commercial anti-helmintic drugs (see: J Helminth (1987) 60, 271).

Secondly, test drugs (Compounds 2, 3, 4, 7,. 8, 9 and 12 of Table 1) were tested using parasites, medium and drug. An immediate response was elicited for Compounds 4, 8, and 9 after one day. After 2–3 days, Compounds 2, 7, and 12 had also reduced motility to less than 1, except for Compound 3 which performed poorly, However, between 4 and 7 days, all the tested Compounds had completely immobilized the worms. Under these conditions, commercial anti-helminthic drugs and artemisinin also cut motility by some 30–40%. Arteether also reduced motility to 4 and 2, after 4 and 7 days respectively.

(b) assessed by tetrazolium colorimetric test

A suitable colorimetric assay uses formation of formazan, a blue dye, from tetrazolium cation generated by 3-[4,5-diethylthiazol-2-yl]-2,4-diphenyltetrazolium bromide (J Helminth (1987) 60, 271). Firstly, Compounds 1, 2, 4, 5, 7, 8, 9, 11 and 12, along with artemisinin and arteether were tested using parasites, medium, cells and test drug. Artemisinin was ineffective, and all the test Compounds performed better than arteether, which caused about 40% inhibition of formazan formation. In fact, all these tested Compounds caused more than 50% inhibition at $5\times 10^{-5}$ M. Compounds 9, 11 and 12 gave more than 90% inhibition.

Secondly, Compounds 2, 3, 4, 7, 8, 9, and 12, artemisinin and arteether were tested using parasites, medium and test drugs. Arteether was ineffective, artemisinin inhibited about 25%, and except for Compound 3, all the test Compounds inhibited formazan formation to a degree better than 80%.

Further Example 3: activity against *Leishmania donovani*

Some of the Compounds were tested against mouse peritoneal macrophages infected with mastigotes of *Leishmania donovani* HU3 according to a published protocol (J Antimicrobial Chemoth (1984) 14, 463).

At 30 mM, activity in the range 35 to 97% inhibition was shown by four drugs, namely Compounds 1, 2, 7 and 10. Other Compounds were less active. One drug, Compound 1, -showed high activity (70% Inhibition) at 10 mM. This compound had an ED$_{50}$ of around 4.5 mm.

I claim:

1. A pharmaceutical composition which comprises a 1,2,4-trioxane derivative of formula:

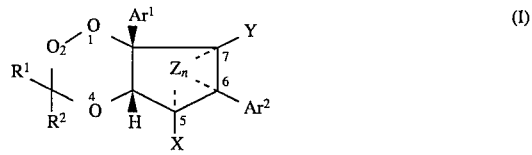

wherein the subscript n is equal to 0 or 1;

the symbol Z represents an epoxide oxygen atom at the 5,6 or 6,7 positions, or a pair of electrons forming a double bond at the 5,6 or 6,7 positions;

each of the symbols Ar$^1$ and Ar$^2$, being the same or different, represents an aromatic group which is phenyl, naphthyl or pyridyl, said aromatic group being unsubstituted or substituted with one or more substituents chosen from alkyl groups, a phenyl group, alkoxy groups, a hydroxy group, halogen atoms, carboxy groups, optionally alkyl-substituted amino groups or alkoxycarbonyl groups;

each of the symbols R$^1$ and R$^2$, being the same or different, represents a linear or branched alkyl group, or R$^x$ and R$^2$, taken together with the carbon atom to which they are attached, form an alicyclic group of 3 to 7 carbon atoms which is optionally interrupted by one oxygen, sulphur or nitrogen atom and which group is optionally substituted with one or more substituents chosen from alkyl groups, a phenyl group, alkoxy groups, a hydroxy group, halogen atoms, carboxy groups, optionally alkyl-substituted amine groups or alkoxycarbonyl groups;

X represents a hydrogen atom, a hydroxy group, a hydroperoxy group; an oxo group or a carbonyloxy group selected from o-fluorobenzoyloxy, isopropoxyearbonyloxy and isopentanoyloxy; and Y is hydrogen:

with the exclusion of the following compounds;
   the compound of formula (I) wherein n is 1; Z is a 5:6 double bond; Ar$^1$ and A$^2$ are both phenyl: R$^1$ R$^2$ are both methyl; X and Y are hydrogen;
   the compound of formula (I) wherein n is 1; Z is a 5,6 double bond; Ar$^1$ and Ar$^2$ are both phenyl; R$^1$ and R$^2$ together form a group —(CH$_2$)$_4$—; X and Y are hydrogen;
   the compound of formula (I) wherein n is 1; Z is a 5,6 or a 6,7 double bond; Ar$^1$ and Ar$^2$ are both phenyl; R$^1$ and R$^2$ are both methyl; X is —OOH and Y is hydrogen; and
   the compound of formula (I) wherein n is 1; Z is a 5,6 or 6,7 double bond; Ar$^1$ and Ar$^3$ are both phenyl; R$^1$ and R$^2$ are both methyl; X is —OH and Y is hydrogen;

together with a pharmaceutically acceptable carrier.

2. The pharmaceutical composition of claim 1, when formulated for parenteral administration.

3. The pharmaceutical composition of claim 1, when formulated as a suspension in oil.

4. The pharmaceutical composition of claim 1, when formulated for oral administration.

5. The pharmaceutical composition of claim 1, when formulated for as a tablet.

6. The pharmaceutical composition of claim 1, wherein X and Y both represent a hydrogen atom.

7. The pharmaceutical composition of claim 6, wherein n is 1 and Z represents a pair of electrons forming a double bond at the 5,6 or 6,7 positions.

8. The pharmaceutical composition of claim 1, wherein Z represents a double bond at the 5,6-position, giving a compound of formula:

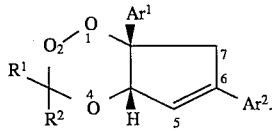

9. The pharmaceutical composition of claim 8, wherein R$^1$ and R$^2$ with the adjacent carbon form a spiropentane or spirohexane, where R$^1$ and R$^2$ respectively are —(CH$_2$)$_4$— or (CH$_2$)$_5$—.

10. The pharmaceutical composition of claim 9, wherein Ar$^1$ and Ar$^2$ represent a phenyl group substituted with one or more chlorine or fluorine atoms.

11. A 1,2,4-trioxane of the formula:

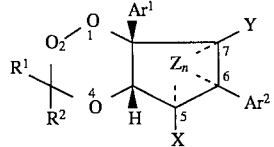

wherein the subscript n is equal to 0 or 1;

the symbol Z represents an epoxide oxygen atom at the 5,6 or 6,7 positions, or a pair of electrons forming a double bond at the 5,6 or 6,7 positions;

each of the symbols Ar$^1$ and Ar$^2$, being the same or different, represents an aromatic group which is phenyl, naphthyl or pyridyl, said aromatic group being unsubstituted or substituted with one or more substituents chosen from alkyl groups, a phenyl group, alkoxy groups, a hydroxy group, halogen atoms, carboxy groups, optionally alkyl-substituted amino groups or alkoxycarbonyl groups;

each of the symbols R$^1$ and R$^2$, being the same or different, represents a linear or branched alkyl group, or R$^1$ or R$^2$, taken together with the carbon atom to which they are attached, form an alicyclic group of 3 to 7 carbon atoms which is optionally interrupted by one oxygen, sulphur or nitrogen atom and which group is optionally substituted with one or more substituents chosen from alkyl groups, a phenyl group, alkoxy groups, a hydroxy group, halogen atoms, carboxy groups, optionally alkyl-substituted amino groups or alkoxycarbonyl groups;

X represents a hydrogen atom, a hydroxy group, a hydroperoxy group, an oxo group of a carbonyloxy group selected from o-fluorobenzoyloxy. isoproxycarbonyloxy and isopentanoyloxy; and Y is hydrogen;

with the exclusion of the following compounds:
   the compound of formula (I) wherein n is 1; Z is a 5,6 double bond; Ar$^1$ and Ar$^2$ are both phenyl; R$^1$ and R$^2$ are both methyl; X and Y are hydrogen;
   the compound of formula (I) wherein n is 1; Z is a 5,6 double bond; Ar$^1$ and Ar$^2$ are both phenyl; R$^1$ and R$^2$ together form a group —(CH$_2$)$_4$—; X and Y are hydrogen;
   the compound of formula (I) wherein n is 1; Z is a 5,6 or a 6,7 double bond; Ar$^1$ and Ar$^2$ are both phenyl; R$^1$ and R$^2$ are both methyl; X is —OOH and Y is hydrogen; and
   the compound of formula (I) wherein n is 1; Z is a 5.6 or a 6,7 double bond; Ar$^1$ and Ar$^2$ are both phenyl; R$^1$ and R$^2$ are both methyl; X is —OH and Y is hydrogen.

12. A method of treatment of malaria, which comprises administering an anti-malarial effective amount of a pharmaceutical composition as defined in claim 1.

* * * * *